United States Patent
Olson

(10) Patent No.: US 9,050,210 B2
(45) Date of Patent: Jun. 9, 2015

(54) LAMINAR DRESSINGS, SYSTEMS, AND METHODS FOR APPLYING REDUCED PRESSURE AT A TISSUE SITE

(71) Applicant: KCI Licensing, Inc., San Antonio, TX (US)

(72) Inventor: Jonathan Scott Olson, Houston, TX (US)

(73) Assignee: KCI Licensing, Inc., San Antonio, TX (US)

( * ) Notice: Subject to any disclaimer, the term of this patent is extended or adjusted under 35 U.S.C. 154(b) by 232 days.

(21) Appl. No.: 13/728,648

(22) Filed: Dec. 27, 2012

(65) Prior Publication Data

US 2013/0116640 A1 May 9, 2013

Related U.S. Application Data

(63) Continuation of application No. 12/560,998, filed on Sep. 16, 2009, now Pat. No. 8,357,131.

(60) Provisional application No. 61/098,000, filed on Sep. 18, 2008, provisional application No. 61/098,015, filed on Sep. 18, 2008.

(51) Int. Cl.
*A61M 1/00* (2006.01)
*A61F 13/02* (2006.01)
(Continued)

(52) U.S. Cl.
CPC ....... *A61F 13/0206* (2013.01); *A61F 13/00987* (2013.01); *A61F 13/02* (2013.01);
(Continued)

(58) Field of Classification Search
CPC ......... A61F 13/00; A61F 13/02; A61F 13/53; A61M 1/00; A61M 27/00; A61M 35/00
USPC .................. 602/41, 42, 44–47; 604/304, 313
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
(Continued)

*Primary Examiner* — Melanie Hand

(57) ABSTRACT

A system for applying a reduced pressure at a tissue site includes a reduced pressure source, a porous pad in fluid communication with the reduced pressure source, and a drape positionable over the porous pad to seal the porous pad at the tissue site. The porous pad includes a plurality of channel walls to form a plurality of channels between the channel walls. The channel walls are substantially liquid impermeable to prevent movement of a liquid through the channel walls but are gas permeable to allow movement of a gas through the channel walls as reduced pressure is applied at the tissue site. The liquid impermeability of the channel walls and the application of reduced pressure causes flow of the liquid to occur through the plurality of channels.

46 Claims, 3 Drawing Sheets

(51) Int. Cl.
*A61F 13/00* (2006.01)
*A61M 27/00* (2006.01)

(52) U.S. Cl.
CPC ............... A61F2013/00174 (2013.01); *A61F 2013/00217* (2013.01); *A61F 2013/00246* (2013.01); *A61F 2013/00412* (2013.01); *A61F 2013/00536* (2013.01); *A61F 2013/00885* (2013.01); *A61F 2013/00914* (2013.01); *A61M 1/0088* (2013.01); *A61M 27/00* (2013.01); *A61F 13/00068* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |
| 2007/0265586 A1 | 11/2007 | Joshi et al. | |
| 2008/0167593 A1* | 7/2008 | Fleischmann | 602/48 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment:

(56) References Cited

OTHER PUBLICATIONS

Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Đukie, Ž. Maksimović, Đ. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

\* cited by examiner

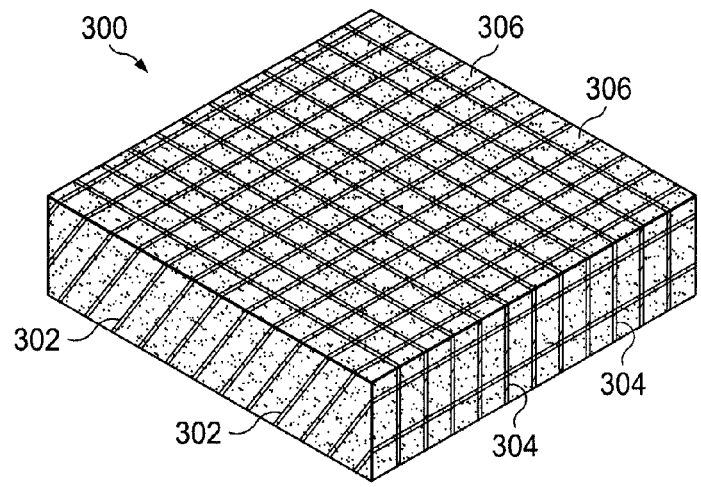
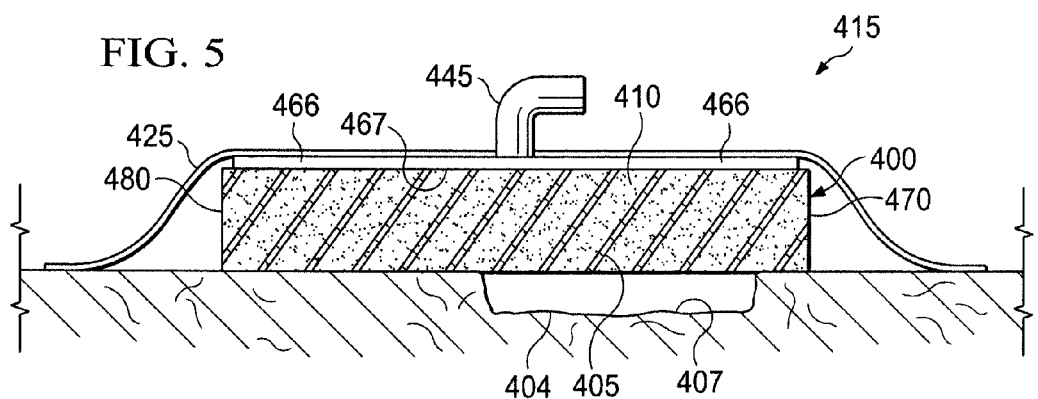
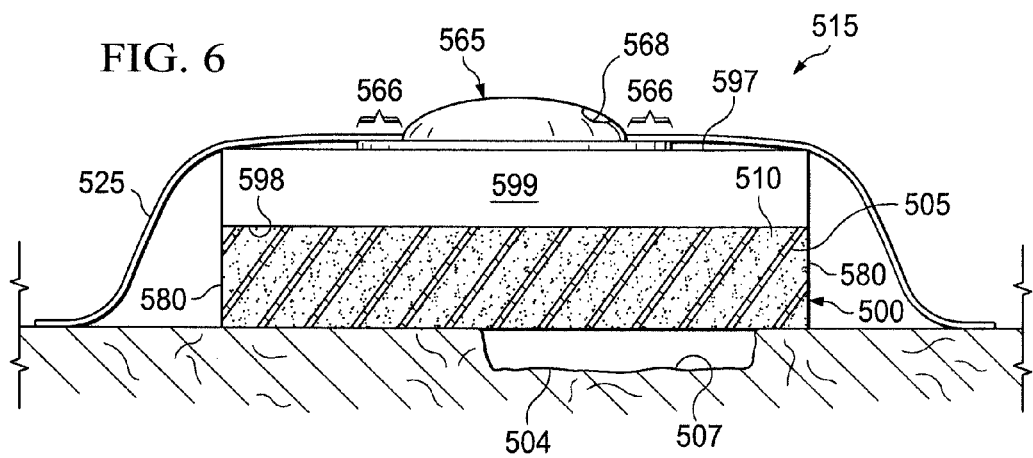

LAMINAR DRESSINGS, SYSTEMS, AND METHODS FOR APPLYING REDUCED PRESSURE AT A TISSUE SITE

CROSS-REFERENCE TO RELATED APPLICATIONS

This application is a continuation of U.S. Non-Provisional application Ser. No. 12/560,998 filed Sep. 16, 2009 which claims the benefit of U.S. Provisional Application No. 61/098,000, filed Sep. 18, 2008, and U.S. Provisional Application No. 61/098,015, filed Sep. 18, 2008. Both of these applications are hereby incorporated by reference.

BACKGROUND

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. In many instances, wound exudate and other liquids from the tissue site are collected within a canister to prevent the liquids from reaching the reduced pressure source.

BRIEF SUMMARY

The problems presented by existing reduced pressure systems and reduced pressure dressings are solved by the systems and methods of the illustrative embodiments described herein. In one illustrative embodiment, a system for applying a reduced pressure at a tissue site is provided. The system includes a reduced pressure source operable to supply reduced pressure and a porous pad in fluid communication with the reduced pressure source. The porous pad includes a plurality of channel walls to form a plurality of channels between the channel walls, and the channel walls are gas permeable to allow movement of a gas through the channel walls as reduced pressure is applied at the tissue site. The channel walls are substantially liquid impermeable to prevent movement of a liquid through the channel walls. The liquid impermeability of the channel walls and the application of reduced pressure causes flow of the liquid to occur through the plurality of channels. The system further includes a drape positionable over the porous pad to seal the porous pad at the tissue site such that reduced pressure can be maintained at the tissue site.

In another embodiment, a system for applying a reduced pressure at a tissue site includes a reduced pressure source operable to supply reduced pressure and a laminar layer in fluid communication with the reduced pressure source. A sealing member covers at least a portion of the laminar layer. The laminar layer includes a plurality of channel walls that form a plurality of channels through which liquid is drawn. The laminar layer is operable to transfer reduced pressure to the tissue site through the plurality of channel walls.

In still another embodiment, a system for applying a reduced pressure at a tissue site includes a reduced pressure source operable to supply reduced pressure and a laminar layer in fluid communication with the reduced pressure source. A drape is positionable over the laminar layer to seal the laminar layer at the tissue site such that reduced pressure can be maintained at the tissue site. The laminar layer includes a plurality of channel walls to form a plurality of channels between the channel walls. The channel walls are substantially liquid impermeable and gas permeable. The channel walls are parallel to one another and form an angle of between about 20 degrees and about 90 degrees with a skin surface adjacent the tissue site.

In yet another embodiment, a dressing for applying a reduced pressure at a tissue site includes a laminar layer having a plurality of channel walls that form a plurality of channels through which liquid is drawn. The laminar layer is operable to transfer reduced pressure to the tissue site through the plurality of channel walls. A sealing member covers at least a portion of the laminar layer to provide a seal over the tissue site.

In another embodiment, a dressing for applying a reduced pressure at a tissue site includes a porous pad having a plurality of channel walls to form a plurality of channels between the channel walls. The channel walls are gas permeable to allow movement of a gas through the channel walls as reduced pressure is applied at the tissue site. The channel walls are substantially liquid impermeable to prevent movement of liquid through the channel walls. The liquid impermeability of the channel walls and the application of reduced pressure causes flow of the liquid to occur through the plurality of channels. A drape is positionable over the porous pad to seal the porous pad at the tissue site such that reduced pressure can be maintained at the tissue site.

In still another embodiment, a dressing for applying a reduced pressure at a tissue site includes a laminar layer having a plurality of channel walls to form a plurality of channels between the channel walls. The channel walls are substantially liquid impermeable and gas permeable. The channel walls are parallel to one another and form an angle of between about 20 degrees and about 90 degrees with a skin surface adjacent the tissue site. A drape is positionable over the laminar layer to seal the laminar layer at the tissue site such that reduced pressure can be maintained, at the tissue site.

In another embodiment, a method for protecting tissue adjacent a tissue site during application of reduced pressure treatment to the tissue site is provided. The method includes applying a dressing having substantially liquid impermeable and gas permeable channel walls to the tissue site. A gas is moved away from the tissue site through the channel walls, and a liquid is moved away from the tissue site between the channel walls.

In yet another embodiment, a method for applying a reduced pressure at a tissue site includes applying a laminar layer to the tissue site. The laminar layer includes a plurality of channel walls that form a plurality of channels through which liquid is capable of being drawn. The laminar layer is capable of transferring reduced pressure to the tissue site through the plurality of channel walls when placed under reduced pressure. The method further includes covering at least a portion of the laminar layer with a sealing member to provide a seal over the tissue site. A reduced pressure is applied to the laminar layer.

In another embodiment, a method of manufacturing a dressing for applying a reduced pressure at a tissue site is provided. The method includes forming a laminar layer having a plurality of channel walls that form a plurality of channels through which liquid is capable of being drawn. The laminar layer is operable to transfer reduced pressure to the tissue site through the plurality of channel walls.

Other features and advantages of the illustrative embodiments will become apparent with reference to the drawings and detailed description that follow.

BRIEF DESCRIPTION OF THE DRAWINGS

FIG. 4 illustrates a schematic, perspective view of an illustrative laminar layer for use in or as a dressing;

FIG. 5 illustrates a schematic cross-sectional view of an illustrative system for applying reduced pressure at a tissue site; and FIG. 6 illustrates a schematic cross-sectional view of an illustrative system for applying reduced pressure at a tissue site.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
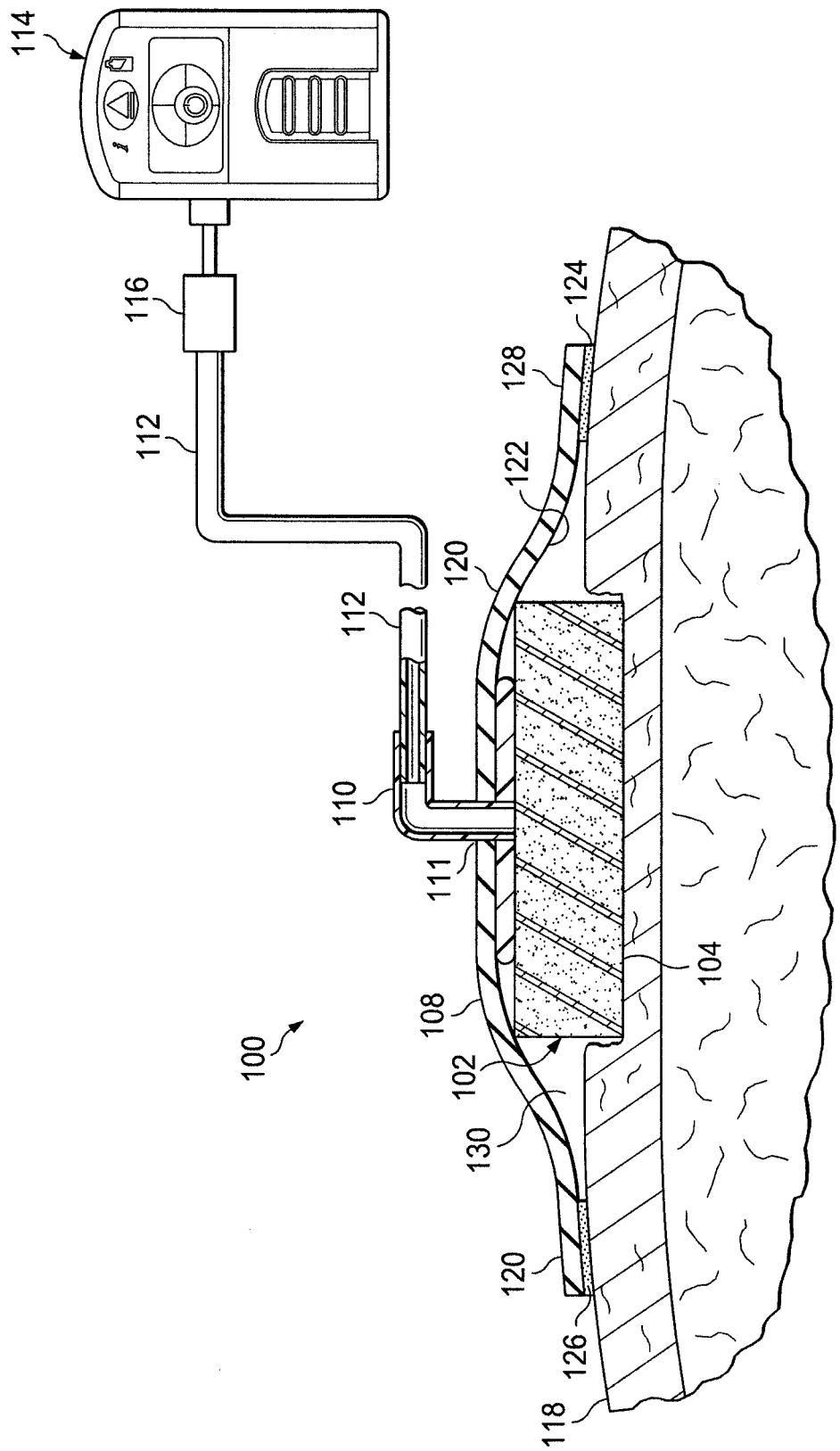
FIG. 1 illustrates a schematic diagram, with a portion in cross section, of an illustrative system for applying reduced pressure at a tissue site.

Referring now primarily to FIG. 1, an illustrative reduced pressure treatment system 100, which includes a laminar dressing 102, or laminar layer, and which applies reduced pressure to a tissue site 104, is presented. The laminar dressing 102 may further include a sealing member 108 and a reduced-pressure connector 110, or connection member. The laminar dressing 102 may help reduce or avoid maceration of tissue adjacent tissue site 104 such as epidermis 118.

The laminar dressing 102 serves as a manifold for distributing reduced pressure. The term "manifold" as used herein generally refers to a substance or structure that is provided to assist in applying reduced pressure to, delivering fluids to, or removing fluids from a tissue site. The manifold typically includes a plurality of flow channels or pathways to improve distribution of fluids provided to and removed from the tissue site. The laminar dressing 102 that serves as a manifold may include a number of layers as will be described further below.

The tissue site 104 may be the bodily tissue of any human, animal, or other organism, including bone tissue, adipose tissue, muscle tissue, neural tissue, dermal tissue, vascular tissue, connective tissue, cartilage, tendons, ligaments, or any other tissue. While the tissue site 104 may include a wound, diseased tissue, or defective tissue, the tissue site 104 may also be healthy tissue that is not wounded, diseased, or defective.

The application of reduced pressure to the tissue site 104 may be used to promote the drainage of exudate and other liquids from the tissue site 104, as well as to stimulate the growth of additional tissue. In the case in which the tissue site 104 is a wound site, the growth of granulation tissue and removal of exudates and bacteria promotes healing of the wound. The application of reduced pressure to non-wounded or non-defective tissue, including healthy tissue, may be used to promote the growth of tissue that may be harvested and transplanted to another tissue location.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. The reduced pressure delivered may be static or varied (patterned or random) and may be delivered continuously or intermittently. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Consistent with the use herein, increases in reduced pressure or vacuum pressure typically refer to a relative reduction in absolute pressure, while decreases in reduced pressure typically refer to an increase in absolute pressure.

Unless otherwise indicated, as used herein, "or" does not require mutual exclusivity.

The reduced pressure is provided to the reduced-pressure connector 110 by a reduced-pressure delivery conduit 112. The reduced-pressure delivery conduit 112 receives reduced pressure from a reduced-pressure source 114. The reduced-pressure source 114 may be any device or subsystem for supplying reduced pressure, including but not limited to a manually operated pump, a powered vacuum pump, a wall vacuum source, or any other device or system capable of supplying a reduced pressure. While the amount and nature of reduced pressure applied to a site will typically vary according to the application, the reduced pressure will typically be between about −5 mm Hg and about −500 mm Hg and more typically between about −100 mm Hg and about −200 mm Hg. In one illustrative embodiment, the reduced pressure source 114 may be a battery-driven vacuum pump. In this example, the pump may use low amounts of power and be capable of operating for an extended period of time on a single charge of the battery.

One or more devices may be fluidly coupled between the reduced-pressure connector 110 and the reduced-pressure source 114. For example, representative device 116 is shown fluidly coupled on a portion of the reduced-pressure delivery conduit 112. The representative device 116 may be a fluid reservoir, or collection member, to hold exudates and other fluids removed. Other illustrative, non-limiting examples of devices 116 that may be included on the reduced-pressure delivery conduit 112 or otherwise fluidly coupled to the reduced-pressure delivery conduit 112 include, without limitation, a pressure sensing or feedback device, a volume detection system, a blood detection system, an infection detection system, a flow monitoring system, or a temperature monitoring system. Some of these devices may be integrally associated with the reduced-pressure source 114 or other aspects of the system 100.

The laminar dressing 102 is adapted to contact or cover the tissue site 104 that is to be treated. As used herein, the term "cover" includes partially or fully covering. Also, a first object that covers a second object may directly or indirectly touch the second object, or may not touch the second object at all.

The laminar dressing 102 is covered fully or partially by the sealing member 108. The sealing member 108 may be any material that provides a fluid seal over the laminar dressing 102 and a portion of a patient's epidermis 118 or the tissue surrounding the tissue site 104. The sealing member 108 may, for example, be an impermeable or semi-permeable, elastomeric material. "Elastomeric" means having the properties of an elastomer. Generally, an elastomer is a polymeric material that has rubber-like properties. More specifically, most elastomers have elongation rates greater than 100% and a significant amount of resilience. The resilience of a material refers to the material's ability to recover from an elastic deformation. Examples of elastomers, which may be used in a sealing member, include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. In an illustrative embodiment, the sealing member 108 may be a drape such as those drapes used with surgical and other medical procedures. Specific examples of drapes may include a silicone drape, a 3M Tegaderm® drape, an acrylic drape such as one available from Avery Dennison, or any other drape or cover.

The sealing member 108 may be provided in "sheet" form, or in a pourable or sprayable form that is applied over the laminar dressing 102 after placement of the laminar dressing 102 adjacent or in contact with the tissue site 104. Similarly, the sealing member 108 may include a device that is placed over the laminar dressing 102 and the tissue site 104 to provide sealing functionality, including but not limited to, a suction cup, a molded cast, or a bell jar. The sealing member 108 has a first side 120 and a second, tissue-facing side 122.

An attachment device 124 may be used to hold the sealing member 108 against the patient's epidermis 118 or another layer, such as a gasket or additional sealing member. The attachment device 124 may take numerous forms. For example, the attachment device 124 may be a medically acceptable, pressure-sensitive adhesive 126 that extends about a periphery, or perimeter, 128 of the sealing member 108.

In one embodiment, the sealing member 108 is configured to provide a sealed connection with the epidermis 118 or the tissue surrounding the laminar dressing 102 and the tissue site 104. The sealed connection may be provided by the adhesive 126 positioned along the perimeter 128 of the sealing member 108, or on any portion of the sealing member 108, to secure the sealing member 108 to the laminar dressing 102 or the tissue surrounding the tissue site 104. The adhesive 126 may be pre-positioned on the sealing member 108 or may be sprayed or otherwise applied to the sealing member 108 immediately prior to installing the sealing member 108. Prior to the application of the sealing member 108 to the tissue site 104, the adhesive 126 may also be covered by an adhesive support layer or removable backing. The adhesive support layer may provide rigidity to the sealing member 108 prior to application and may also aid in the actual application of the sealing member 108 onto the tissue site 104 or tissue near the tissue site 104. The adhesive support layer may be peeled off or otherwise removed before applying.

The reduced-pressure connector 110 allows fluid communication between the reduced-pressure source 114 and an interior space 130 formed between the second, tissue-facing side 122 of the sealing member 108 and the tissue site 104. In one embodiment, the reduced-pressure connector 110 may pass through an aperture 111 in the sealing member 108 or be otherwise coupled to the sealing member 108. In another embodiment, the reduced-pressure delivery conduit 112 may directly couple the reduced-pressure source 114 to the laminar dressing 102.

The reduced-pressure delivery conduit 112 may be any tube, conduit, or flow path through which a gas, liquid, gel, or other fluid may flow. The possible embodiments of the reduced-pressure delivery conduit 112 are numerous, and non-limiting examples follow. The reduced-pressure delivery conduit 112 may have any cross-sectional shape, such as a circle, oval, polygon, or any other shape. In addition, the reduced-pressure delivery conduit 112 may be made from any material, and may be either flexible or inflexible. In FIG. 1, the reduced-pressure connector 110 couples reduced-pressure delivery conduit 112 to the representative device 116, and the reduced-pressure source 114. However, reduced-pressure delivery conduit 112 may instead directly couple reduced pressure source 114 to the laminar dressing 102. Also, the reduced-pressure delivery conduit 112 may include one or more paths or lumens through which fluid may flow. For example, the reduced-pressure delivery conduit 112 may include two lumens with one lumen being used to monitor pressure to determine the amount of reduced pressure being applied at the tissue site 104. The other lumen may be used to deliver fluids, such as air, antibacterial agents, antiviral agents, cell-growth promotion agents, irrigation fluids, or other chemically active agents, to the tissue site 104. A fluid source from which these fluids may originate is not shown in FIG. 1.

The reduced-pressure connector 110 permits the passage of a fluid (such as exudates, air, etc.) from the laminar dressing 102 to reduced-pressure delivery conduit 112, and vice versa. In another illustrative embodiment (not shown), the reduced pressure treatment system 100 does not include the reduced-pressure connector 110. In this illustrative embodiment, the reduced-pressure delivery conduit 112 may be inserted directly into the sealing member 108 or the laminar dressing 102 such that an end of the reduced-pressure delivery conduit 112 is adjacent to or in contact with the sealing member 108 or any of the laminar dressing 102 in a manner that allows for the delivery of reduced pressure.

The reduced-pressure connector 110 may be located anywhere relative to the laminar dressing 102. For example, although FIG. 1 shows the reduced-pressure connector 110 and the opening or aperture 111 in the sealing member 108 through which the reduced-pressure connector 110 extends as being centrally located relative to the laminar dressing 102, the reduced-pressure connector 110 and the opening or aperture 111 may be located adjacent to the edges of the laminar dressing 102. Although not preferred, the reduced-pressure connector 110 or reduced-pressure delivery conduit 112 may instead be inserted beneath the sealing member 108 at periphery 128.

In operation, the laminar dressing 102 is deployed on the tissue site 104 and reduced pressure is delivered to the tissue site 104. More specifically, the laminar dressing 102 is deployed proximate the tissue site 104 where treatment is desired. The sealing member 108 is positioned over the laminar dressing 102 and at least a portion of the patient's epidermis 118 to form the sealed space 130. If not already provided in the sealing member 108, the aperture 111 may be formed in the sealing member 108 and the reduced-pressure connector 110 applied. The reduced-pressure delivery conduit 112 is fluidly coupled to the reduced-pressure connector 110 and to the reduced-pressure source 114. The reduced-pressure source 114 is activated and reduced pressure is delivered to the tissue site 104.

Figure 2:
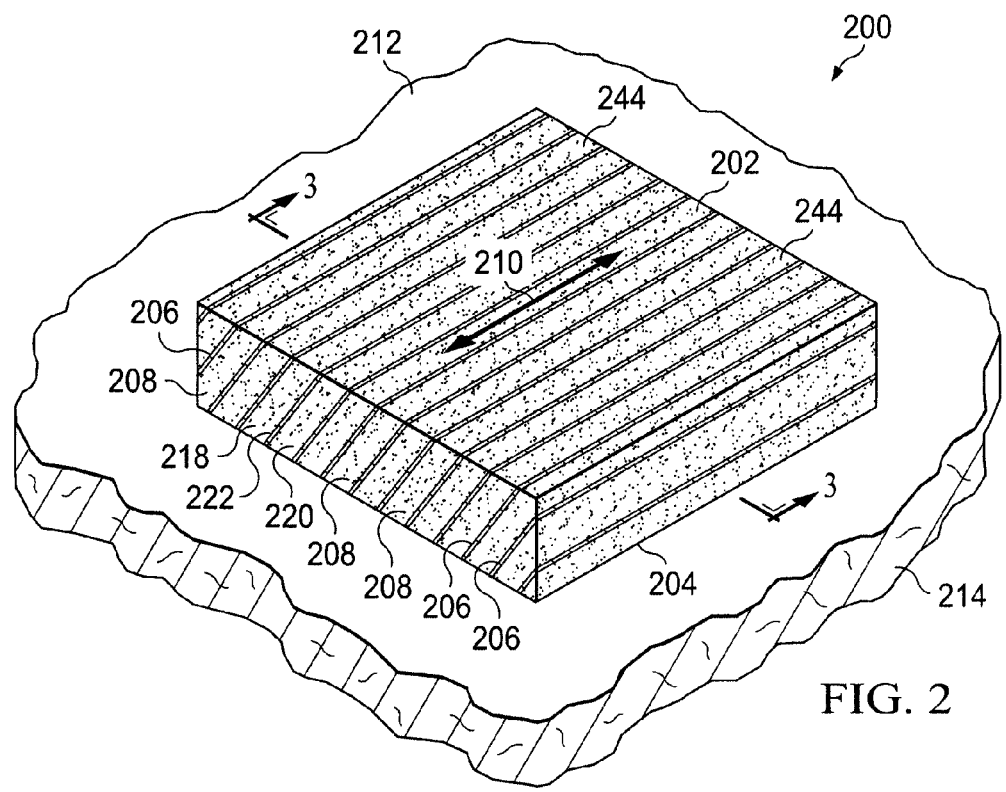
FIG. 2 illustrates a schematic, perspective view of an illustrative laminar layer for use in or as a dressing.
Figure 3:
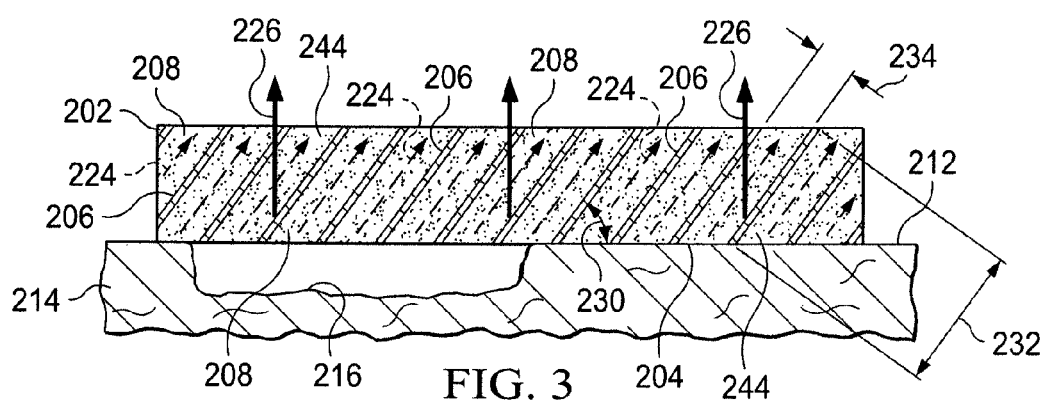
FIG. 3 illustrates a schematic, cross-sectional view of the illustrative laminar layer of FIG. 2.

Referring now primarily to FIGS. 2 and 3, an illustrative laminar layer 200 is presented that may be included in a dressing or may be used as a dressing. In one illustrative example, the laminar layer 200 is the only layer in a dressing.

The laminar layer 200 has a first side 202 and a second, tissue-facing side 204. The laminar layer 200 includes a plurality of channel walls 206 that form a plurality of channels 208. In the illustrative example of FIG. 2, the channel walls 206 are substantially parallel to one another and extend longitudinally in one direction parallel to an axis indicated by an arrow 210. However, in other embodiments, the channel walls 206 may extend along any number of directions, and may intersect one another at various points in the laminar layer 200. An illustrative example of a laminar layer in which the channel walls intersect is provided below in FIG. 4.

In the illustrative embodiment of FIGS. 2 and 3, the channels 208 are also angled or slanted relative to a surface 212, which may be planar, of the epidermis 214 or other tissue at or near a tissue site 216. At least two channels in the plurality of channels 208 share a common channel wall of the plurality of channel walls 206. For example, a first channel 218 and a second channel 220 of the plurality of channels 208 each share common channel wall 222 of the plurality of channel walls 206. In one embodiment, each of the channels 208 shares a respective common channel wall of the plurality of channel walls 206 with another channel in the plurality of channels 208. In another embodiment, the channels 208 may not share common channel walls.

In one embodiment, the channel walls 206 are made from or include a material that is gas permeable and substantially liquid impermeable. In one example, the channel walls 206 are composed of expanded poly(tetrafluoroethylene), such as a Gore-Tex® material. In another example, the channel walls 206 are composed of poly(tetrafluoroethylene). The material or materials from which the laminar layer 200 is composed may also be elastic so that the laminar layer 200 better conforms to the shape and topology of the surface of the tissue site 216.

The channels 208 may serve to segregate and direct liquid flow away from the tissue site 216, yet reduce or substantially prevent lateral migration of liquid through the laminar layer 200. More specifically, the laminar layer 200 may reduce or substantially prevent liquid, such as exudate, from spreading along an interface between the laminar layer 200 and the tissue site 216. This benefit of the laminar layer is enhanced further when the laminar layer manifolds reduced pressure.

Referring now primarily to FIG. 3, a cross-sectional view of the laminar layer 200 is presented. The cross-sectional view of the laminar layer 200 illustrates that flow directions for liquids and gases may be different when reduced pressure is applied to the laminar layer 200 using a reduced pressure source, such as the reduced pressure source 114 in FIG. 1. The gas directional flow 226 is shown in this illustrative embodiment as being substantially normal to the planar surface 212 of the tissue, e.g., epidermis 214, near the tissue site 216. The liquid directional flow 224 flows within the channels 208.

The differing direction of flow between the liquid flow 224 and the gas flow 226 is caused, at least in part, by the material from which the channel walls 206 are composed. In the embodiment illustrated in FIG. 3, the channel walls 206 are gas permeable and substantially liquid impermeable so that gas, such as air, may be drawn through the channel walls 206, while liquid (e.g., exudates) from the tissue site 216 is restricted or cannot pass through the channel walls 206. In this way, reduced pressure from a reduced pressure source, such as reduced pressure source 114 in FIG. 1, may be distributed through the channel walls 206 such that a gas is drawn through the channel walls 206. As a result, reduced pressure is transferred to the tissue site 216 through the channel walls 206. Also, liquid, such as exudate from the tissue site 216, is drawn through at least a portion of the channels 208 to a desired location for processing or storage—including possible storage by another layer of the dressing. The segregated directional flow of the gas and liquid allow efficient application of reduced pressure and substantially prevent or reduce unwanted migration of liquid through the laminar layer 200, which assists in avoiding or reducing maceration of the epidermis 214.

In another embodiment, both the gas and the liquid may flow through the channels 208 in the direction indicated by the liquid flow arrows 224. In such an embodiment, the channel walls 206 may be substantially impermeable to both gas and liquid.

The channel walls 206 may form an angle 230 with the surface 212 at or near the tissue site 216. In the embodiment illustrated in FIGS. 2 and 3, each of the channels 208 also forms the same angle 230 with respect to the surface 212. In one example, the angle 230 is an acute angle. In another example, the angle 230 may be between about 20 degrees and about 90 degrees. In still another embodiment, the angle 230 may be about 45 degrees. Although each of the channel walls 206 and channels 208 are shown to form the same angle with the surface 212, the channel walls 206 and channels 208 may also form different angles with the surface 212 from one another. While the angles that the channel walls 206 form with the surface 212 may vary from just greater than 0 degrees up to 90 degrees (i.e. substantially perpendicular to surface 212), the value of angle 230 may determine the compressibility of the laminar layer 200 when subjected to reduced pressure. For example, a laminar layer 200 having channel walls 206 arranged perpendicular to surface 212 will likely result in a laminar layer 200 that is less compressible than one that includes channel walls 206 oriented at 45 degrees. It should also be noted, however, that as the angle 230 approaches 0 degrees, the benefit afforded by the channel walls 206 may be less since the channel walls 206 are less able to prevent lateral migration of liquid through the laminar layer 200.

The channels 208 may have a length 232 and a width 234. The length 232 of any two of the channels 208 may differ from one another or be the same. A portion of the channels 208 may also have the same length or be different. In one example, a majority of the channels 208 have a length 232 that exceeds the width 234. In another example, all of the channels 208 have a length 232 that exceeds their width 234. In the example of FIG. 3, each of the channels 208 has the same width 234. However, in other embodiments, the width 234 of each of the channels 208 may also vary from one another. In an illustrative embodiment, the width 234 of the channels, and thus the distance between the channel walls 206, is between about 1 mm and about 2 mm. In still another embodiment, the width 234 is greater than or equal to about 1 mm.

The thickness of the channel walls 206 may vary depending on the material from which the wall is constructed. The thickness of each channel wall 206 may be uniform or may vary relative to other channel walls 206 in a particular laminar layer 200. In one illustrative embodiment, the thickness of each of the plurality of channel walls 206 is between about 0.25 mm and about 0.5 mm.

Although the laminar layer 200 is shown to have a rectangular cross-sectional shape, the laminar layer 200 may have any cross-sectional shape. For example, any or all of the corners or edges of the laminar layer 200 may be rounded. Such a rounded configuration may ensure a better fit between the laminar layer 200 and a sealing member, such as sealing member 120 in FIG. 1. The cross-sectional shape of the laminar layer 200 may be square, circular, elliptical, polygonal, or any other shape that allows the laminar layer 200 to distribute reduced pressure.

A biasing member 244 may be positioned between the channel walls 206 to substantially prevent collapse of the channels 208 when the laminar layer 200 is subjected to compressive forces caused by the application of reduced pressure. The biasing member 244 may exert a biasing force on the channel walls 206 during compression of the laminar layer 200 to allow continued liquid flow through the channels 208. In the embodiment illustrated in FIGS. 2 and 3, the biasing member 244 may be a porous foam that is positioned between the channel walls 206. In one embodiment, the porous foam may be an open-cell, reticulated foam such as, for example, a polyurethane foam or a polyvinyl alcohol (PVA) foam. In other embodiments, the biasing member 244 may be a corrugated material, a spring, or any other material or device that is capable of preventing total collapse of the channels 208 and allowing continued flow of liquids through the channels 208.

While the laminar layer 200 has been described as having a plurality of channel walls 206 with biasing members 244 positioned within the channels 208 between the channel walls 206, the laminar layer 200 may alternatively be described as a porous pad that includes a plurality of channel walls 206 and channels 208. In this embodiment, the porous material of the porous pad would serve as a biasing member to prevent total collapse of the channels 208. The porous material of the porous pad may be an open-cell, reticulated foam such as polyurethane, polyvinyl alcohol, or any other suitable material.

Referring now primarily to FIG. 4, an illustrative laminar layer 300 is presented. While analogous in many respects to the laminar layer 200 of FIGS. 2 and 3, the laminar layer 300 not only includes a first plurality of channel walls 302 but also includes a second plurality of channel walls 304 that extend along a direction that is substantially perpendicular to the first plurality of channel walls 302. Although the second channel walls 304 are perpendicular to the first channel walls 302 in this illustrative embodiment, the second channel walls 304 may form any angle with the first channel walls 302. Also, although channel walls 302 and 304 are shown to be straight, the channel walls 302 and 304 may be curved in shape, including circular or elliptical shapes.

The intersection of the channel walls 302 and 304 in the laminar layer 300 forms rectangular-shaped channels 306. However, the channels 306 formed by the channel walls 302 and 304 may have any shape, including a polygonal, triangular, circular, elliptical, or any other shape. Liquid from a tissue site may be drawn through the channels 306 using reduced pressure.

Referring now primarily to FIG. 5, a dressing 415, which includes laminar layer 400, is shown according to an illustrative embodiment. The dressing 415 includes a sealing member 425, which covers the laminar layer 400. In the example illustrated in FIG. 5, the laminar layer 400 is the only layer in the dressing material that is covered by the sealing member 425. Reduced pressure is transferred from a reduced pressure source, such as the reduced pressure source 114 in FIG. 1, to the tissue site 404 via the laminar layer 400, as well as via a connection member 445.

The connection member 445 has a flange portion 466 that is disposed between the sealing member 425 and the laminar layer 400. The flange portion 466 of the connection member 445 may extend substantially across the entire width of the laminar layer 400. A tissue facing side 467 of the flange portion 466 may be adjacent to the laminar layer 400, and the flange portion 466 may have an opening that faces the laminar layer 400. The extension of the flange portion 466 across the entire width of the laminar layer 400 may facilitate a more even distribution of reduced pressure across the laminar layer 400 and better reception of liquid from the laminar layer 400 into the connection member 445. However, the flange portion 466 may have any width relative to the laminar layer 400.

Also, the sealing member 425 may conform to the shape of the laminar layer 400. Although a space is shown between the sealing member 425 and sides 480 of the laminar layer 400, the sealing member 425 may also touch the sides 480 of the laminar layer 400.

In one example, liquid, such as exudate, from the wound site 407 may be drawn through the channels 410 of the laminar layer 400. The liquid may be drawn through the channels 410 of the laminar layer 400 using reduced pressure that is distributed through the channel walls 405 of the laminar layer 400. The liquid, upon passing through the channels 410, may be drawn into the connection member 445. The liquid may then be transferred into a delivery tube, such as the reduced-pressure delivery conduit 112 in FIG. 1.

Referring now primarily to FIG. 6, a dressing 515, which includes laminar layer 500, is shown according to an illustrative embodiment. The dressing 515 further includes a connection member 565 having flange portion 566, a sealing member 525, and an absorbent layer 599. The absorbent layer 599 is positioned adjacent to the laminar layer 500. The absorbent layer 599 both distributes reduced pressure that is transferred to the dressing 515, and absorbs liquid from the tissue site 105 via the laminar layer 500.

The absorbent layer 599 may be one or more layers that absorb liquid. The absorbent layer 599 has a first side 597 and a second, tissue-facing side 598. At least a portion of the second, tissue-facing side 598 of the absorbent layer 599 abuts the laminar layer 500. The absorbent layer 599 may have any thickness relative to the laminar layer 500. In one embodiment, the absorbent layer 599 may be thicker than the laminar layer 500, but alternatively, the absorbent layer 599 may be thinner than the laminar layer 500.

The sealing member 525 may conform to the shape of the absorbent layer 599 and laminar layer 500. For example, although a space is shown between the sealing member 525 and the sides 580 of the laminar layer 500, the sealing member may also touch sides 580 of the laminar layer 500.

In one example, liquid, such as exudate, from the wound site 507 may be drawn through channels 510 of the laminar layer 500. The liquid may be drawn through the channels 510 of the laminar layer 500 using reduced pressure that is distributed through channel walls 505 of the laminar layer 500. The reduced pressure may be transferred to the dressing 515 via a delivery tube, which may be inserted into the connection member 565 using a slot 568 in the connection member 565. The liquid from the tissue site 504, upon passing through the channels 510, may be drawn into the absorbent layer 599. The liquid may be stored in the absorbent layer 599, thereby eliminating the need for an external fluid collection apparatus.

The laminar layers 200, 300, 400, 500 described herein are each illustrated as being positioned above, but not in contact with, the tissue site. While this may be a preferred arrangement of the laminar layer in some embodiments, in other embodiments it may be desirable to place at least a portion of the laminar layer in direct contact with the tissue site. In still other embodiments, it may be desirable to place a separate porous pad or other manifold between the tissue site and the laminar layer.

While the laminar layers described herein often include a porous foam with a plurality of channel walls, the laminar layer could alternatively be formed from a sheet of material that is substantially liquid impermeable and gas permeable. The sheet of material may preferably include holes, apertures, slits, or other openings that are positioned in the sheet of material to act as channels for liquids drawn through the laminar layer by reduced pressure. The liquid impermeable, gas permeable material would act as channel walls to allow better transmission of gas during the application of reduced pressure. In one illustrative embodiment, the material from which the laminar layer is formed may be expanded polytetrafluoroethylene (ePTFE), or any other material that is substantially liquid impermeable and gas permeable.

The dressings and laminar layers described herein may be used as part of a process or method for protecting tissue adjacent a tissue site from maceration and other damage during application of reduced pressure treatment to the tissue site. The method may include applying a dressing having substantially liquid impermeable and gas permeable channel walls to the tissue site. A gas is moved away from the tissue site through the channel walls, and a liquid is moved away from the tissue site between the channel walls. The channel walls serve to substantially prevent the liquid from spreading along an interface between the dressing and the tissue adjacent the tissue site.

In another illustrative embodiment, a method for applying a reduced pressure at a tissue site may include applying a laminar layer to the tissue, the laminar layer having a plurality of channel walls that form a plurality of channels through which liquid is capable of being drawn. The laminar layer is capable of transferring reduced pressure to the tissue site through the plurality of channel walls when placed under reduced pressure. A portion of the laminar layer is covered with a sealing member to provide a seal over the tissue site, and a reduced pressure is applied to the laminar layer.

In yet another illustrative embodiment, a method of manufacturing a dressing for applying a reduced pressure to a tissue site is provided. The method includes forming a laminar layer having a plurality of channel walls that form a plurality of channels through which liquid is capable of being drawn. The laminar layer is operable to transfer reduced pressure to the tissue site through the plurality of channel walls. At least a portion of the laminar layer may be covered with a sealing member.

Although several illustrative embodiments and advantages have been disclosed herein, it should be understood that various changes, substitutions, permutations, and alterations can be made without departing from the scope of the invention as defined by the appended claims. It will be appreciated that any feature that is described in a connection to any one embodiment may also be applicable to any other embodiment.

I claim:

1. A system for applying a reduced pressure at a tissue site, the system comprising:
   a reduced pressure source operable to supply reduced pressure;
   a porous pad in fluid communication with the reduced pressure source, the porous pad having a plurality of channel walls forming a plurality of channels through the porous pad, the channel walls being gas permeable and substantially liquid impermeable, and an open-cell, reticulated foam positioned between the plurality of channel walls to exert a biasing force on the channel walls; and
   a drape positionable over the porous pad to seal the porous pad at the tissue site such that reduced pressure can be maintained at the tissue site.

2. The system of claim 1 further comprising a delivery tube operable to transfer reduced pressure between the reduced pressure source and the laminar layer.

3. The system of claim 1, wherein the plurality of channels are parallel to one another.

4. The system of claim 1, wherein:
   the plurality of channel walls are parallel to one another; and
   each of the plurality of channel walls forms an angle of about 45 degrees with a surface of the porous pad adapted to be placed adjacent the tissue site.

5. The system of claim 1, wherein:
   the plurality of channel walls are parallel to one another; and
   a distance between each channel wall of the plurality of channel walls and an adjacent channel wall is greater than or equal to about 1 mm.

6. The system of claim 1, wherein:
   the plurality of channel walls are parallel to one another; and
   a distance between each channel wall of the plurality of channel walls and an adjacent channel wall is between about 1 mm and about 2 mm.

7. The system of claim 1, wherein the thickness of each of the plurality of channel walls is between about 0.25 mm and about 0.5 mm.

8. The system of claim 1, wherein the plurality of channel walls include expanded polytetrafluoroethylene.

9. The system of claim 1, wherein a cross-sectional shape of each of the plurality of channels is one of a square, triangle, or circle.

10. The system of claim 1, wherein each of the plurality of channels shares a respective common channel wall in the plurality of channel walls with another channel in the plurality of channels.

11. The system of claim 1, wherein a length of each of the plurality of channels exceeds a width of each of the plurality of channels.

12. The system of claim 1, further comprising an absorbent layer adjacent to the porous pad, wherein the absorbent layer is adapted to absorb liquid from the tissue site via the plurality of channels.

13. The system of claim 1, wherein the channel walls of the porous pad are adapted to substantially prevent the liquid from spreading along an interface between the porous pad and the tissue site.

14. A dressing for applying a reduced pressure at a tissue site, the dressing comprising:
   a laminar layer having a plurality of parallel channel walls that form a plurality of channels through the laminar layer; and a biasing member positioned between at least two of the plurality of channel walls.

15. The dressing of claim 14, further comprising a sealing member covering at least a portion of the laminar layer to provide a seal over the tissue site.

16. The dressing of claim 14, wherein the biasing member comprises a porous foam positioned between the plurality of channel walls.

17. The dressing of claim 16, wherein the porous foam is an open-cell, reticulated foam.

18. The dressing of claim 14, wherein the plurality of channel walls are a plurality of gas permeable channels walls.

19. The dressing of claim 14, wherein the plurality of channel walls are liquid impermeable.

20. The dressing of claim 14, wherein the plurality of channel walls are impermeable to exudate from the tissue site.

21. The dressing of claim 14, wherein:
each of the plurality of channel walls forms an angle of between about 20 degrees and about 90 degrees with a surface of the laminar layer adapted to be positioned adjacent the tissue site.

22. The dressing of claim 14, wherein:
each of the plurality of channel walls forms an angle of about 45 degrees with a surface of the laminar layer adapted to be positioned adjacent the tissue site.

23. The dressing of claim 14, wherein:
a distance between each channel wall of the plurality of channel walls and an adjacent channel wall is greater than or equal to about 1 mm.

24. The dressing of claim 14, wherein:
a distance between each channel wall of the plurality of channel walls and an adjacent channel wall is between about 1 mm and about 2 mm.

25. The dressing of claim 14, wherein the thickness of each of the plurality of channel walls is between about 0.25 mm and about 0.5 mm.

26. The dressing of claim 14, wherein the plurality of channel walls include expanded polytetrafluoroethylene.

27. The dressing of claim 14, wherein a cross-sectional shape of each of the plurality of channels is one of a square, triangle, or circle.

28. The dressing of claim 14, wherein each of the plurality of channels shares a respective common channel wall in the plurality of channel walls with another channel in the plurality of channels.

29. The dressing of claim 14, wherein a length of each of the plurality of channels exceeds a width of each of the plurality of channels.

30. The dressing of claim 14, further comprising an absorbent layer adjacent to the laminar layer, wherein the absorbent layer is adapted to absorb liquid from the tissue site via the plurality of channels.

31. The dressing of claim 14, further comprising a porous pad positioned between the tissue site and the laminar layer.

32. The dressing of claim 14, wherein the laminar layer is adapted to substantially prevents fluid from spreading along an interface between the laminar layer and the tissue site.

33. A dressing for applying a reduced pressure at a tissue site, the dressing comprising:
a porous pad having a plurality of channel walls forming a plurality of channels between the channel walls, the channel walls being gas permeable and substantially liquid impermeable;
a biasing member positioned between at least two of the plurality of channel walls; and
a second porous pad adapted to be positioned between the tissue site and the first porous pad.

34. The dressing of claim 33, further comprising a drape positionable over the porous pad to seal the porous pad at the tissue site such that reduced pressure can be maintained at the tissue site.

35. The dressing of claim 33, wherein the biasing member comprises an open-cell, reticulated foam.

36. The dressing of claim 33, wherein the plurality of channels are parallel to one another.

37. The dressing of claim 33, wherein:
the plurality of channel walls are parallel to one another; and
each of the plurality of channel walls forms an angle of about 45 degrees with a surface of the porous pad.

38. The dressing of claim 33, wherein:
the plurality of channel walls are parallel to one another; and
a distance between each channel wall of the plurality of channel walls and an adjacent channel wall is greater than or equal to about 1 mm.

39. The dressing of claim 33, wherein:
the plurality of channel walls are parallel to one another; and
a distance between each channel wall of the plurality of channel walls and an adjacent channel wall is between about 1 mm and about 2 mm.

40. The dressing of claim 33, wherein the thickness of each of the plurality of channel walls is between about 0.25 mm and about 0.5 mm.

41. The dressing of claim 33, wherein the plurality of channel walls include expanded polytetrafluoroethylene.

42. The dressing of claim 33, wherein a cross-sectional shape of each of the plurality of channels is one of a square, triangle, or circle.

43. The dressing of claim 33, wherein at least two channels in the plurality of channels share a common channel wall in the plurality of channel walls.

44. The dressing of claim 33, wherein a length of each of the plurality of channels exceeds a width of each of the plurality of channels.

45. The dressing of claim 33, further comprising an absorbent layer adjacent to the porous pad, wherein the absorbent layer is adapted to absorb liquid from the tissue site via the plurality of channels.

46. The dressing of claim 33, wherein the channel walls of the porous pad are adapted to substantially prevent fluid from spreading along an interface between the porous pad and the tissue site.

* * * * *